US006861217B1

(12) United States Patent
Liggett

(10) Patent No.: US 6,861,217 B1
(45) Date of Patent: Mar. 1, 2005

(54) VARIATION IN DRUG RESPONSE RELATED TO POLYMORPHISMS IN THE $\beta_2$-ADRENERGIC RECEPTOR

(75) Inventor: Stephen B. Liggett, Cincinnati, OH (US)

(73) Assignees: Genaissance Pharmaceuticals, Inc., New Haven, CT (US); University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/856,803

(22) PCT Filed: Nov. 24, 1999

(86) PCT No.: PCT/US99/27963

§ 371 (c)(1),
(2), (4) Date: May 25, 2001

(87) PCT Pub. No.: WO00/31307

PCT Pub. Date: Jun. 2, 2000

Related U.S. Application Data

(60) Provisional application No. 60/109,886, filed on Nov. 25, 1998.

(51) Int. Cl.[7] .............................. C12Q 1/68; C12P 19/34; C07H 21/04
(52) U.S. Cl. ........................ 435/6; 435/91.1; 435/91.2; 536/23.5
(58) Field of Search ...................... 435/6, 91.2, 91.1; 536/23.1, 23.5, 24.31, 24.33

(56) References Cited

U.S. PATENT DOCUMENTS

| | | | |
|---|---|---|---|
| 5,442,049 A | | 8/1995 | Anderson et al. |
| 5,573,910 A | | 11/1996 | Deretc et al. |
| 5,589,331 A | | 12/1996 | Nielsen et al. |
| 5,700,907 A | | 12/1997 | Hercend et al. |
| 5,817,477 A | * | 10/1998 | Soppet et al. ............... 435/65.1 |
| 6,087,485 A | * | 7/2000 | Brooks-Wilson ........... 536/23.5 |
| 2003/0039979 A1 | | 2/2003 | Drysdale et al. |

FOREIGN PATENT DOCUMENTS

| | | | |
|---|---|---|---|
| WO | 97/35973 | * | 10/1997 |
| WO | WO 97/35973 | | 10/1997 |
| WO | 99/37761 | * | 7/1999 |

OTHER PUBLICATIONS

Edmorine et al. Proceedings of the National Academy of Sciences, USA. (1987) 84: 6995–6999.*
Timmermann et al. Kidney International. Jun. 1998. 55: 1455–1460.*
Schofield. GenBank Accession No. Y00106, Sep. 1993.*
Timmermann et al. Human Mutation (Mar. 1998) 11(4): 343–344.*
Timmermann. Journal of Molecular Medicine. May 1998. 76: B30, Abstract P–109.*
Large (Journal of Clinical Investigation (1997) 100: 3005–3013.*
New England Biolabs Catalog. 1995, p. 38.*
Green, S.A., J. Turki, P. Bejarano, I.P. Hall, and S.B. Liggett, "Influence of b2–adrenergic receptor genotypes on signal transduction in human airway smooth muscle cells," American Journal of Respiratory Cell and Molecular Biology, vol. 13, p. 25–33, 1995.
Hall, I.P., A. Wheatley, P. Wilding, and S.B. Liggett, "Association of the Glu27 b2–adrenoceptor polymorphism with lower airway reactivity in asthmatic subjects," Lancet, vol. 345, p. 1213–1214, 1995.
Liggett, S.B., "Polymorphisms in the B2–Adrenergic Receptor and Asthma," American Journal of Repsiratory and Critical Care Medicine, vol. 156, p. S156–S162, 1997.
Martinez, F.D., P.E. Graves, M. Baldini, S. Solomon, and R. Erickson, "Association between genetic polymorphisms of the beta2–adrenoceptor and response to albuterol in children with and without a history of wheezing," Journal of Clinical Investigation, vol. 100, p. 3184–3188, 1997.
McGraw, D.W., S. Forbes, L. Kramer, and S.B. Liggett, "Polymorphisms in the 5' Leader Cistron of the Human Beta2–Adrenergic Receptor Regulate Receptor Expression," Journal of Clinical Investigation, vol. 102, p. 1927–32, 1998.
Parola, A.L. and B.K. Kobilka, "The peptide product of a 5' leader cistron in the beta 2 adrenergic receptor mRNA inhibits receptor synthesis," Journal of Biological Chemistry, vol. 269, p. 4497–4505, 1994.
Turki, J., J. Lorenz, S.A. Green, E.T. Donnelly, M. Jacinto, and S. Liggett, "Myocardial Signaling Defects and Imparied Cardiac Function of a Human B2–Adrenergic Receptor Polymorphism Expressed in Transgenic Mice," Proceedings of the National Academy of Sciences, vol. 93, p. 10483–88, 1996.
Turki, J., J. Pak, S.A. Green, R.J. Martin, and S. Liggett, "Genetic Polymorphisms of the B2–Adrenergic Receptor in Nocturnal and Nonnocturnal Asthma," Journal of Clinical Investigation, vol. 95, p. 1635–1641, 1995.
Yamada K, et al., "Polymorphism in the 5'–leader cistron of the beta2–adrenergic receptor gene associated with obesity and type 2 diabetes," Journal of Clinical Endocrinology & Metabolism, vol. 84, p. 1754–1757, 1999.

* cited by examiner

Primary Examiner—Carla J. Myers
(74) Attorney, Agent, or Firm—Melodie W Henderson; Matthew M Catlett

(57) ABSTRACT

A novel polymorphic site in the 5' leader cistron of the $\beta_2$-adrenergic receptor ($\beta_2$AR) gene is disclosed. The polymorphisms present at this site result in different levels of inhibition of translation of $\beta_2$AR mRNA. Compositions and methods for genotyping this polymorphic site as disclosed. In addition, methods for using this genotype information are disclosed, including predicting genetic predisposition to a disease modified by $\beta_2$AR expression and predicting a patient's bronchodilating response to $\beta_2$-agonists.

2 Claims, 8 Drawing Sheets

```
CCCGGGTTCA AGAGATTCTC CTGTCTCAGC CTCCCGAGTA GCTGGGACTA
CAGGTACGTG CCACCACACC TGGCTAATTT TTGTATTTTT AGTAGAGACA  100
AGAGTTACAC CATATTGGCC AGGATCTTTT GCTTTCTATA GCTTCAAAAT
GTTCTTAATG TTAAGACATT CTTAATACTC TGAACCATAT CAATTTGCCA  200
TTTTGGTAAG TCACAGACGC CAGATGGTGG CAATTTCACA TGGCACAACC
CGAAAGATTA ACAAACTATC CAGCAGATGA AAGGATTTTT TTTAGTTTCA  300
TTGGGTTTAC TGAAGAAATT GTTTGAATTC TCATTGCATC TCCAGTTCAA
CAGATAATGA GTGAGTGATG CCACACTCTC AAGAGTTAAA AACAAAACAA  400
CAAAAAAATT AAACAAAAG CACACAACTT TCTCTCTCTG TCCCAAAATA
CATACTTGCA TACCCCCGCT CCAGATAAAA TCCAAAGGGT AAAACTGTCT  500
TCATGCCTGC AAATTCCTAA GGAGGCACC TAAAGTACTT GACAGCCAGT
GTGCTGAGGA AATCGGCAGC TGTTGAAGTC ACCTCCTGTG CTCTTGCCAA  600
ATGTTTGAAA GGGAATACAC TGGGTTACCG GGTGTATGTT GGGAGGGGAG
CATTATCAGT GCTCGGGTGA GGCAAGTTCG CAGTACCCAG ATGGAGACAT  700
CCGTGTCTGT GTCGCTCTGG ATGCCTCCAA GCCAGCGTGT GTTTACTTTC
TGTGTGTGTC ACCATGTCTT TGTGCTTCTG GGTGCTTCTG TGTTTGTTTC  800
TGGCCGCGTT TCTGTGTTGC ACAGGGGTGA CTTTGTGCCG GATGGCTTCT
GTGTGAGAGC GCGCGCGAGT GTGCATGTCG GTGAGCTGGG AGGGTGTGTC  900
TCAGTGTCTA TGGCTGTGGT TCGTATAAG TCTGAGCATG TCTGCCAGGG
TGTATTTGTG CCTGTATGTG CGTGCCTCGG TGGGCACTCT CGTTTCCTTC  1000
CGAATGTGGG GCAGTGCCGG TGTGCTGCCC TCTGCCTTGA GACCTCAAGC
CGCGCAGGCG CCCAGGGCAG GCAGGTAGCG GCCACAGAAG AGCCAAAAGC  1100
TCCCGGGTTG GCTGGTAAGG ACACCACCTC CAGCTTTAGC CCTCTGGGC
CAGCCAGGGT AGCCGGGAAG CAGTGGTGGC CCGCCCTCCA GGGAGCAGTT  1200
GGGCCCCGCC CGGGCCAGCC CCAGGAGAAG GAGGGCGAGG GGAGGGGAGG
GAAAGGGGAG GAGTGCCTCG CCCCTTCGCG GCTGCCGGCG TGCCATTGGC  1300
CGAAAGTTCC CGTACGTCAC GGCGAGGGCA GTTCCCTAA AGTCCTGTGC
ACATAACGGG CAGAACGCAC TGCGAAGCGG CTTCTTCAGA GCACGGGCTG  1400
GAACTGGCAG GCACCGCGAG CCCCTAGCAC CCGACAAGCT GAGTGTGCAG
GACGAGTCCC CACCACACCC ACACCACAGC CGCTGAATGA GGCTTCCAGG  1500
CGTCCGCTCG CGGCCGCAG AGCCCGCCG TGGGTCCGCC CGCTGAGGCG
CCCCCAGCCA GTGCGCTTAC CTGCCAGACT GCGCGCCATG GGGCAACCCG  1600
GGAACGGCAG CGCCTTCTTG CTGGCACCCA ATAGAAGCCA TGCGCCGGAC
CACGACGTCA CGCAGCAAAG GGACGAGGTG TGGGTGGTGG GCATGGGCAT  1700
CGTCATGTCT CTCATCGTCC TGGCCATCGT GTTTGGCAAT GTGCTGGTCA
TCACAGCCAT TGCCAAGTTC GAGCGTCTGC AGACGGTCAC CAACTACTTC  1800
ATCACTTCAC TGGCCTGTGC TGATCTGGTC ATGGGCCTGG CAGTGGTGCC
CTTTGGGGCC GCCCATATTC TTATGAAAAT GTGGACTTTT GGCAACTTCT  1900
GGTGCGAGTT TTGGACTTCC ATTGATGTGC TGTGCGTCAC GGCCAGCATT
GAGACCCTGT GCGTGATCGC AGTGGATCGC TACTTTGCCA TTACTTCACC  2000
TTTCAAGTAC CAGAGCCTGC TGACCAAGAA TAAGGCCCGG GTGATCATTC
TGATGGTGTG GATTGTGTCA GGCCTTACCT CCTTCTTGCC CATTCAGATG  2100
CACTGGTACC GGGCCACCCA CCAGGAAGCC ATCAACTGCT ATGCCAATGA
GACCTGCTGT GACTTCTTCA CGAACCAAGC CTATGCCATT GCCTCTTCCA  2200
TCGTGTCCTT CTACGTTCCC CTGGTGATCA TGGTCTTCGT CTACTCCAGG
GTCTTTCAGG AGGCCAAAAG GCAGCTCCAG AAGATTGACA AATCTGAGGG  2300
CCGCTTCCAT GTCCAGAACC TTAGCCAGCT GGAGCAGGAT
```

FIGURE 1

ATGAGGCTTC CAGCCGTCCG CTCGCGGCCC GCAGAGCCCC GCCGTGGGTC CGCCTGCTGA

FIGURE 2

MRLPGVRSRPAEPRRGSAC

VARIATION IN DRUG RESPONSE RELATED TO POLYMORPHISMS IN THE β₂-ADRENERGIC RECEPTOR

This application is based on U.S. Provisional Application Ser. No. 60/109,886, filed Nov. 25, 1998.

FIELD OF THE INVENTION

This invention relates to the fields of pharmacogenomics, diagnostics and gene therapy. More specifically, the present invention relates to methods of screening drugs, which modulate the activity of the β₂-adrenergic receptor as well as methods of diagnosing and/or treating diseases involving β₂AR or its isoforms.

BACKGROUND OF THE INVENTION

Studies over the last several years of mutations/polymorphisms in G-protein coupled receptor genes in the human population have revealed several classes of genetic variations. One class is composed of polymorphisms that alter receptor function or expression and are the direct cause of a disease. These diseases are typically rare and the polymorphism is not found in healthy (non-affected) individuals. Examples of this class are polymorphisms of the leutinizing hormone receptor that cause constitutive activation and results in familial male precocious puberty (Themmen, A. P. N. et al., *J Endocrinol* 153:179–183, 1997), the calcium sensing receptor which causes constitutive activation and results in familial hypoparathyroidism (Chattopadhyay, N. et al., *Endocr Rev* 17:289–307, 1996), and the V2 vasopressin receptor that causes depressed receptor function and results in nephrogenic diabetes insipidus (Rosenthal, W. A. et al., *J. Biol. Chem.* 268:13030–13033, 1993).

A second class of genetic variations of G-protein coupled receptors comprises those that alter receptor function or expression but do not appear to be the direct or sole cause of a disease. Here, the variation can be common in apparently healthy individuals. Studies to date indicate that these polymorphisms may act as disease modifiers (Liggett, S. B. 1996. The genetics of 2-adrenergic receptor polymorphisms: relevance to receptor function and asthmatic phenotypes. In *The Genetics of Asthma*. S. B. Liggett and D. A. Meyers, editors. Marcel Dekker, New York. 455478) with the physiologic consequences becoming apparent when receptor function is critical for compensation in the diseased state or for the response to therapy. As such, they may be responsible for certain clinical subsets of a given disease (such as different phenotypes of asthma or hypertension) or represent the basis of differential responsiveness to therapeutic agents.

β₂-adrenergic receptors (β₂AR) are G-protein coupled receptors that are activated by endogenous catecholamines. These receptors are widely distributed, and play important roles in regulating cardiac, vascular, pulmonary, and metabolic functions. Studies of such physiologic functions of β₂AR in humans have revealed several observations. First, there appears to be substantial interindividual variation in responsiveness, and secondly receptor function appears to be dynamically regulated as indicated by intraindividual variation. Recently, significant genetic variability in the structure of the β₂AR in the human population due to polymorphisms in the β₂AR gene has been delineated (1, 2). These polymorphisms are located 46, 79, 100 and 491 bases downstream of the ATG start codon, and result in variation that occurs in the amino-terminus of the receptor at amino acids 16 (Arg or Gly), 27 (Gln or Glu) and 34 (Val or Met) and in the fourth transmembrane spanning domain at amino acid 164 (Thr or Ile). In recombinant cell studies (3, 4), and in primary cultures of cells endogenously expressing these variants (5), clear phenotypic differences have been shown between the polymorphic receptors. The Gly16 receptor was found to undergo enhanced agonist-promoted downregulation of receptor number as compared to the Arg16 receptor (3). In contrast, the Glu27 receptor was found to undergo very little agonist-promoted downregulation compared to the Gln27 receptor (3). These variants are common in the population (1). The Ile164 receptor, which occurs in the heterozygous state in 5% of the population, displays depressed coupling to the stimulatory G protein, $G_s$ (4).

Subsequent studies have assessed the role of the aforementioned polymorphic β₂AR in diseases such as asthma [reviewed in (6)], based on the role of β₂AR in modulating bronchial smooth muscle tone. In these studies, no differences in the frequencies of any of these polymorphisms between non-asthmatics and asthmatics have been reported. However, polymorphisms at positions 16 and 27 were found to act as significant disease modifiers (7–10). In the majority of the above cited studies, the presumption has been that the clinical phenotypes of those with the Gly16 polymorphism were due to enhanced downregulation of this receptor (as compared to those with the Arg16 receptor) by endogenous catecholamines. Thus responsiveness to β-agonists in individuals with this polymorphism has been considered depressed due to this tonic downregulation. A similar scenario is considered in individuals with the Glu27 variant, who exhibit greater responsiveness to β-agonists than those individuals with the Gln7 receptor, presumably due to its minimal downregulation by catecholamines. An amplification of these differences may occur during chronic agonist administration, as has recently been shown in asthma (11).

The β₂AR is encoded by an intronless gene on chromosome 5q31 (12). Receptor transcripts have a 5' leader region harboring an open reading frame (ORF) that encodes a 19 amino acid peptide (13). Recent in vivo and in vitro studies have shown that this peptide impedes translation of β₂AR mRNA, and thus regulates cellular expression of the receptor (14). Given the importance of this 5' leader cistron in controlling β₂AR expression, this region in the human population was examined for genetic variability.

A Summary of the Invention

The present invention is based on the discovery of a common polymorphism that is located in the 5' leader cistron (5'LC) of the β₂AR gene. In particular, a polymorphism of cytosine or thymine located 47 bases upstream of the β₂AR coding block results in either Arg or Cys being encoded at the terminal amino acid (position 19) of the 5'LC peptide (Arg19Cys) (see FIGS. 1–3; SEQ ID NOS:1–3, respectively). The inventor herein has also discovered that a substitution of Cys for Arg in the 5'LC peptide results in increased expression of β₂AR in both recombinant and airway smooth muscle cells, which endogenously express β₂AR. Thus, it is believed this β₂AR 5' LC polymorphic site represents, at least in part, the genetic basis of variable physiologic sympathetic responses, variation in disease phenotypes, and differences in the therapeutic efficacy of β-agonists and p-antagonists.

Thus, in one aspect the present invention provides methods and compositions for genotyping and haplotyping the β₂AR gene of an individual. In one embodiment, a genotyping method comprises isolating from the individual a nucleic acid mixture comprising the two copies of the β₂AR gene present in the individual and determining the identity of the nucleotide pair at the 5'LC polymorphic site in the two copies to assign a β₂AR genotype to the individual. The haplotyping method comprises isolating from the individual a nucleic acid molecule containing only one of the two copies of the β₂AR gene, or a fragment thereof, that is present in the individual and determining in that copy the identity of the nucleotide at the 5'LC PS and at one or more additional β₂AR polymorphic sites. Compositions useful in performing the genotyping and haplotyping methods include oligonucleotide probes and primers designed to specifically hybridize to a target region containing the 5'LC polymorphic site. These genotyping methods and compositions are useful for studying the effect of the 5'LC polymorphisms in the etiology of various diseases and efficacy of drugs targeting the β₂AR.

In another embodiment, the invention provides a method for detecting which variant(s) of the 5'LC peptide is expressed in an individual. The method comprises contacting a biological sample from the individual with a first antibody that specifically recognizes and binds to only one of the β₂AR 5'LC peptide variants and detecting a complex formed with the first antibody. In a preferred embodiment, the method further comprises contacting the biological sample with a second antibody that specifically recognizes and binds to the other β₂AR 5'LC peptide variant and detecting a complex formed with the second antibody. This method is useful for investigating the effects of the 5'LC peptide variants on β₂AR expression. In addition, the preferred embodiment is useful to determine the genotype. If both antibodies react with the sample, the individual is heterozygous C/T at the 5'LC polymorphic site.

Another aspect of the invention is based on the discovery that β₂AR alleles carrying the 5'LC C polymorphism are most likely to also have the polymorphisms which encode Gln and Arg at amino acids 16 and 27, respectively. Thus, the genotype for the 5'LC polymorphic site may be used to predict the identity of the genotype for one or both of these β₂AR coding block polymorphisms.

In yet another embodiment, the invention provides a method for identifying an association between a β₂AR 5'LC genotype and a trait. The method comprises comparing the frequency of the β₂AR 5'LC genotype in a population exhibiting the trait with the frequency of the genotype in a reference population, wherein a higher frequency of the genotype in the trait population than in the reference population indicates the trait is associated with the genotype. Such methods have applicability in developing diagnostic tests and therapeutic treatments for a variety of diseases, including arrhythmia, heart failure, hypertension, vascular disease, migraine, asthma, chronic obstructive pulmonary disease (COPD), anaphylaxis, obesity, diabetes and premature labor.

The present invention also provides a method for predicting an individual's genetic predisposition to a disease modified by the β₂AR. The method comprises determining the individual's genotype for the 5'LC polymorphic site. If the individual is homozygous T, increased β₂AR expression is likely and the individual has an increased risk for diseases affected by too much β₂AR expression. If the individual is homozygous C, decreased β₂AR expression is likely and the individual has an increased risk for diseases affected by too little β₂AR expression. In a preferred embodiment, the disease modified by the β₂AR is selected from the group consisting of arrhythmia, heart failure, hypertension, vascular disease, migraine, asthma, chronic obstructive pulmonary disease (COPD), anaphylaxis, obesity, diabetes and premature labor.

The present invention further provides methods for predicting a patient's response to β-agonist therapy for bronchospasm, which typically occurs in asthma, COPD and anaphylaxis. In one embodiment, the method comprises determining the genotype of the 5'LC polymorphic site in the patient's β₂AR gene. If the patient is homozygous for the T polymorphism, failure to respond to a β-agonist is likely, while a patient is likely to respond if he or she is homozygous for the C polymorphism or is heterozygous T/C at this site. Thus, knowledge of a patient's β₂AR 5'LC genotype provides a physician with information useful for making determinations as to which drug to administer, drug dosages, and duration of treatment.

BRIEF DESCRIPTION OF THE FIGURES

FIG. 1 illustrates a partial DNA sequence for one allele of the human β₂AR gene (SEQ ID NO:1), with the boxed region indicating the ORF for the 5' leader cistron, the underline indicating the start codon for the ORF encoding the β₂AR protein (also referred to herein as the β₂AR coding block), and the location of the novel polymorphic site described herein indicated in bold.

FIG. 2 illustrates the DNA sequence of the β₂AR 5' leader cistron containing the thymidine polymorphism (SEQ ID NO:2) at nucleotide 55 instead of the cytosine polymorphism shown in FIG. 1.

FIG. 3 illustrates the amino acid sequence of the Cys variant of the β₂AR 5' leader cistron peptide (SEQ ID NO:3).

DESCRIPTION OF THE PREFERRED EMBODIMENTS

Figure 4A:
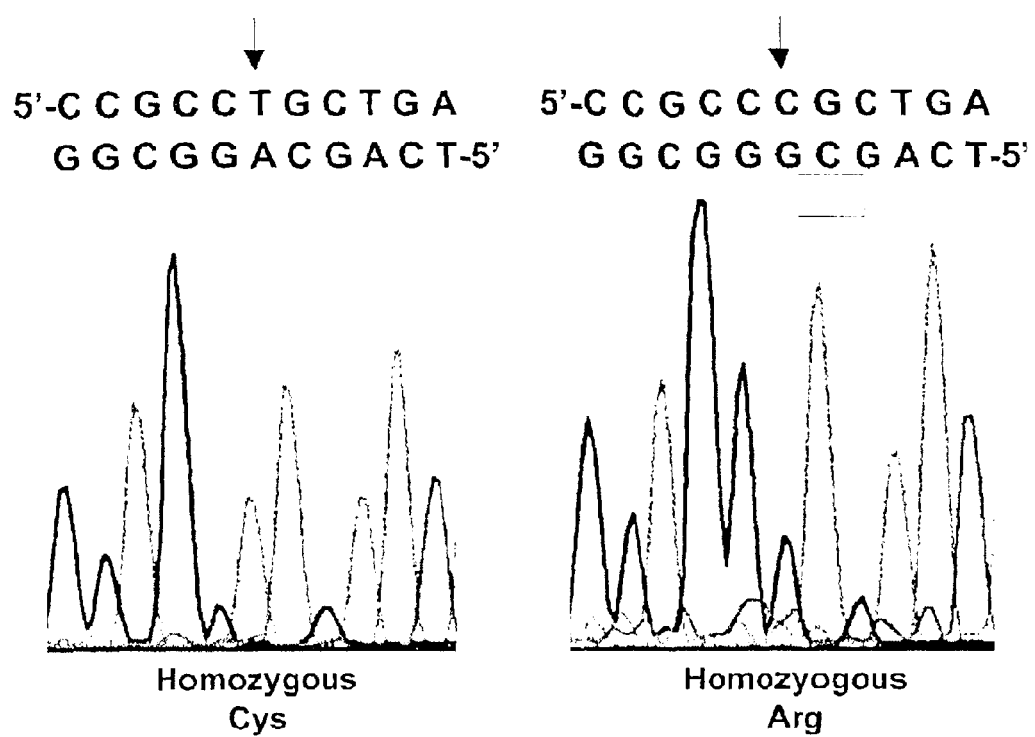
FIG. 4 illustrates identification of the polymorphic site in the 5' leader cistron of the human β₂AR gene, with FIG. 4A showing representative antisense sequencing results from two homozygous individuals and FIG. 4B showing representative restriction digests of a 163 bp PCR product digested with MspAII.

In accordance with the present invention, the inventor herein has discovered a common polymorphism of C or T in the 5' leader cistron of the β₂AR gene. The C allele of this polymorphism encodes Arg at position 19 of the 5'LC peptide (MRLPGVRSRPAEPRRGSAR) (SEQ ID NO:4) while the T allele encodes Cys at this position (MRLPGVRSRPAEPRRGSAC) (SEQ ID NO:3). As demonstrated in the Examples below, β₂AR expression is significantly increased in cells homozygous for the T allele as compared to cells homozygous for the C allele. The studies described herein also show that the polymorphism probably does not affect transcription of the $\beta_2AR$ gene, which is consistent with an earlier study that concluded that the 5'LC peptide inhibits translation (14). In addition, the examples below demonstrate that the 5'LC C polymorphism is in linkage disequilibrium with the $\beta_2AR$ coding block polymorphisms that encode Arg16 and Gln27. Because the =$\beta_2AR$ is expressed in virtually every tissue of the body, it is believed an individual's genotype for the 5'LC polymorphism of the present invention has the potential to influence, or be a marker of, his or her genetic predisposition for various diseases, including asthma, hypertension, congestive heart failure, ischemic heart disease, arrhythmia, obesity, diabetes, vascular disease, and premature labor.

In the context of this disclosure, the following terms shall be defined as follows unless otherwise indicated:

Allele—A particular form of a genetic locus, distinguished from other forms by its particular nucleotide or amino acid sequence.

Gene—A segment of DNA that contains all the information for the regulated biosynthesis of an RNA product, including promoters, exons, introns, and other untranslated regions that control expression.

Genotype—An unphased 5' to 3' sequence of nucleotide pair(s) found at one or more polymorphic sites in a locus on a pair of homologous chromosomes in an individual.

Genotyping—A process for determining a genotype of an individual.

Haplotype—A phased 5' to 3' sequence of nucleotides found at two or more polymorphic sites in a locus on a single chromosome from a single individual.

Haplotyping—A process for determining a haplotype of an individual.

Haplotype pair—The two haplotypes found for a locus in a single individual.

Isoform—A particular form of a gene, mRNA, cDNA or the protein encoded thereby, distinguished from other forms by its particular sequence and/or structure.

Isolated—As applied to a biological molecule such as RNA, DNA, oligonucleotide, or protein, isolated means the molecule is for practical purposes free of other biological molecules such as non-desired nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature.

Naturally-occurring—A term used to designate that the object it is applied to, e.g., naturally-occurring polynucleotide or polypeptide, can be isolated from a source in nature and which has not been intentionally modified by man.

Nucleotide pair—The nucleotides found at a polymorphic site on corresponding strands of the two copies of a chromosome in an individual.

Phasing—The description of the identity of the nucleotides at two or more polymorphic sites in the same linear genetic molecule.

Polymorphic site (PS)—A position within a locus at which at least two alternative sequences are found in a population.

Polymorphic variant—A gene, mRNA, cDNA, polypeptide or peptide whose nucleotide or amino acid sequence varies from a reference sequence due to the presence of a polymorphism in the gene.

Polymorphism—The sequence variation observed in an individual at a polymorphic site. Polymorphisms include nucleotide substitutions, insertions, deletions and microsatellites and may, but need not, result in detectable differences in gene expression or protein function.

Polynucleotide—A nucleic acid molecule comprised of single-stranded RNA or DNA or comprised of complementary, double-stranded DNA.

Reference Population—A group of subjects or individuals who are predicted to be representative of the genetic variation found in the general population. In preferred embodiments, the reference population represents the genetic variation in the population at a certainly level of at least 85%, preferably at least 90%, more preferably at least 95% and even more preferably at least 99%.

Single Nucleotide Polymorphism (SNP)—Typically, the specific pair of nucleotides observed at a single polymorphic site. In rare cases, three or four nucleotides may be found.

Treatment—A stimulus administered internally or externally to an individual.

Population Group—A group of individuals sharing a common ethnogeographic origin.

Information on the identity of the $\beta_2AR$ 5'LC polymorphism(s) present in any particular individual as well as the frequency of the two alleles for this polymorphic site in any particular population of individuals is expected to be useful for a variety of basic research and clinical applications. Thus, the invention provides compositions and methods for detecting the $\beta_2AR$ 5'LC polymorphisms described herein.

The compositions comprise oligonucleotide probes and primers capable of hybridizing to a target region containing the 5'LC polymorphic site or defining this target region for amplification. As used herein, the term "oligonucleotide" refers to a polynucleotide molecule having less than about 100 nucleotides. A preferred oligonucleotide of the invention is 10 to 35 nucleotides long. More preferably, the oligonucleotide is between 15 and 30, and most preferably, between 20 and 25 nucleotides in length. The oligonucleotide may be comprised of any phosphorylation state of ribonucleotides, deoxyribonucleotides, and acyclic nucleotide derivatives, and other functionally equivalent derivatives. Alternatively, oligonucleotides may have a phosphate-free backbone, which may be comprised of linkages such as carboxymethyl, acetamidate, carbamate, polyamide (peptide nucleic acid (PNA)) and the like (Varma, R. in *Molecular Biology and Biotechnology A Comprehensive Desk Reference*, Ed. R. Meyers, VCH Publishers, Inc. (1995), pages 617–620). Oligonucleotides of the invention may be prepared by chemical synthesis using any suitable methodology known in the art, or may be derived from a biological sample, for example, by restriction digestion. The oligonucleotides may be labeled, according to any technique known in the art, including the use of radiolabels, fluorescent labels, enzymatic labels, proteins, haptens, antibodies, sequence tags and the like.

Oligonucleotide probes and primers of the invention must be capable of specifically hybridizing to a target region of a β₂AR polynucleotide, i.e., a β₂AR gene, cDNA, or mRNA. As used herein, specific hybridization means the oligonucleotide reacts with the target region with sufficient specificity to allow the skilled artisan to discriminate between hybridization to the target region and hybridization to a non-target region. Preferably, the oligonucleotide specifically hybridizes to the target region under conventional high stringency conditions. The skilled artisan can readily design and test oligonucleotide probes and primers suitable for detecting the β₂AR 5'LC polymorphisms using the information provided herein in conjunction with the known sequence information for the β₂AR gene and routine techniques.

In describing the β₂'LC polymorphic site identified herein, reference is made to the sense strand of the gene for convenience. However, as recognized by the skilled artisan, nucleic acid molecules containing the β₂AR gene may be complementary double stranded molecules and thus reference to a particular site on the sense strand refers as well to the corresponding site on the complementary antisense strand. Thus, reference may be made to either strand and still comprise the same polymorphic site and an oligonucleotide may be designed to specifically hybridize to either strand. Thus, the invention also includes oligonucleotides which are complementary to the sense strand of the β₂AR 5' gene.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, by Sambrook J. et al., in *Molecular Cloning, A Laboratory Manual, 2nd Edition*, Cold Spring Harbor Press, Cold Spring Harbor, N.Y. (1989) and by Haymes, B. D. et al. in *Nucleic Acid Hybridization, A Practical Approach*, IRL Press, Washington, D.C. (1985). While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the oligonucleotide probe or primer as long as the resulting probe or primer is still capable of specifically hybridizing to the target region.

Preferred oligonucleotides of the invention are allele-specific oligonucleotides. As used herein, the term allele-specific oligonucleotide (ASO) means an oligonucleotide that is able, under sufficiently stringent conditions, to specifically hybridize to one allele of the β₂AR 5'LC or other β₂AR locus, at a target region containing a polymorphic site while not hybridizing to the corresponding region in another allele(s). As understood by the skilled artisan, allele-specificity will depend upon a variety of readily optimized stringency conditions, including salt and formamide concentrations, as well as temperatures for both the hybridization and washing steps. Examples of hybridization and washing conditions typically used for ASO probes are found in Kogan et al., "Genetic Prediction of Hemophilia A" in *PCR Protocols, A Guide to Methods and Applications*, Academic Press, 1990 and Ruano et al., 87 *Proc. Natl. Acad. Sci. USA* 6296–6300, 1990. Typically, an allele-specific oligonucleotide will be perfectly complementary to one allele while containing a single mismatch for another allele.

Allele-specific oligonucleotide probes which usually provide good discrimination between different alleles are those in which a central position of the oligonucleotide probe aligns with the polymorphic site in the target region (e.g., approximately the $7^{th}$ or $8^{th}$ position in a 15 mer, the $8^{th}$ or $9^{th}$ position in a 16 mer, the $10^{th}$ or $11^{th}$ position in a 20 mer). A preferred ASO probe for detecting β₂AR 5'LC polymorphisms comprises a nucleotide sequence selected from the group consisting of: 5'-GTCCGCCCGCTGAGG-3' (SEQ ID NO:5) or its complement and 5'-GTCCGCCTGCTGAGG-3' (SEQ ID NO:6) or its complement.

An allele-specific oligonucleotide primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. Allele-specific oligonucleotide primers hybridizing to either the coding or noncoding strand are contemplated by the invention. A preferred ASO forward primer for detecting β₂AR 5'LC polymorphisms comprises a nucleotide sequence selected from the group consisting of 5'-CCCCGCCGTGGGTCCGCCCG-3'(SEQ ID NO:7) and 5'-CCCCGCCGTGGGTCCGCCTG-3'(SEQ ID NO:8). A preferred ASO reverse primer for detecting β₂AR 5'LC polymorphisms comprises a nucleotide sequence selected from the group consisting of 5'-GGCTGGGGGCGCCTCAGCGG-3' (SEQ ID NO:9) and 5'-GGCTGGGGGCGCCTCAGCAG-3'(SEQ ID NO:10).

In some embodiments, a composition contains two or more differently labeled allele-specific oligonucleotides for simultaneously probing the identity of nucleotides at the β₂AR 5'LC polymorphic site and one or more additional polymorphic sites in the β₂AR gene or other locus. It is also contemplated that primer compositions may contain two or more sets of allele-specific primer pairs to allow simultaneous targeting and amplification of two or more regions containing a β₂AR polymorphic site, one of which is the β₂AR 5'LC polymorphic site.

Allele-specific oligonucleotides of the invention may also be immobilized on or synthesized on a solid surface such as a microchip, bead, or glass slide (see, e.g., WO 98/20020 and WO 98/20019). Such immobilized allele-specific oligonucleotides may be used in a variety of polymorphism detection assays, including but not limited to probe hybridization and polymerase extension assays. Immobilized ASO's of the invention may comprise an ordered array of oligonucleotides designed to rapidly screen a DNA sample for polymorphisms in multiple genes at the same time.

In another embodiment, the invention provides a kit comprising at least two allele-specific oligonucleotides for detecting β₂AR 5'LC polymorphisms packaged in separate containers. The kit may also contain other components such as hybridization buffer (where the oligonucleotides are to be used as probes) packaged in another separate container. Alternatively, where the oligonucleotides are to be used to amplify a target region, the kit may also contain, a polymerase and a reaction buffer optimized for primer extension mediated by the polymerase, such as PCR.

These oligonucleotide compositions and kits are useful in methods for genotyping and/or haplotyping the FAR gene in an individual. As used herein the term "β₂AR genotype" means the genotype contains at least the nucleotide pair present at the 5'LC PS and may optionally include the nucleotide pair(s) present at one or more additional polymorphic sites in the $\beta_2$AR gene. Similarly, the term "$\beta_2$AR haplotype" means the haplotype contains the nucleotide present at the 5'LC PS as well as the nucleotide(s) present at one or more additional polymorphic sites in the $\beta_2$AR gene. The additional polymorphic sites in these genotyping and haplotyping may be currently known polymorphic sites or sites that are subsequently discovered. In preferred embodiments, the additional polymorphic sites are located 20 nucleotides upstream of the star codon and coding block polymorphic sites located 46, 79, 100 and 491 nucleotides downstream of the coding block ATG site. These sites are also referred to herein as −20 PS, +46 PS, +79 PS, +100 PS, and +491 PS.

One embodiment of the genotyping method comprises isolating from the individual a nucleic acid mixture comprising the two copies of the $\beta_2$AR gene, or a fragment thereof, that are present in the individual and determining the identity of the nucleotide pair at the 5'LC polymorphic site (5'LC PS) in the two copies in order to assign a $\beta_2$AR genotype to the individual. As will be readily understood by the skilled artisan, the two "copies" of a gene in an individual may be the same allele or may be different alleles. Typically, the nucleic acid mixture is isolated from a biological sample taken from the individual, such as a blood sample or tissue sample. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the $\beta_2$AR gene is expressed. In a preferred embodiment, the $\beta_2$AR genotype also comprises the nucleotide pair at one or more additional polymorphic sites in the $\beta_2$AR gene. If a $\beta_2$AR gene fragment is isolated, it must contain the 5'LC PS and any other $\beta_2$AR sites to be genotyped.

One embodiment of the haplotyping method comprises isolating from the individual a nucleic acid molecule containing only one of the two copies of the $\beta_2$AR gene, or a fragment thereof, that is present in the individual and determining in that copy the identity of the nucleotide at the 5'LC PS and at one or more additional $\beta_2$AR polymorphic sites. In a preferred embodiment, the additional $\beta_2$AR polymorphic site(s) is selected from the group consisting of −20 PS, +46 PS, +79 PS, +100 PS and +491 PS. The nucleic acid may be isolated using any method that allows separation of the two copies of the WAR gene present in an individual. Such methods include targeted in vivo cloning (TIVC) in yeast as described in WO 98/01573, U.S. Pat. No. 5,866,404, and U.S. Pat. No. 5,972,614. As will be readily appreciated by those skilled in the art, any individual clone will provide haplotype information on only one of the two $\beta_2$AR gene copies present in an individual. If haplotype information is desired for the individual's other copy, additional $\beta_2$AR clones will need to be examined. Typically, at least five clones will need to be examined to have more than a 90% probability of haplotyping both copies of the $\beta_2$AR gene in an individual. Another method for separating the two copies of the $\beta_2$AR gene, which is described in U.S. Pat. No. 5,972,614, uses an allele specific oligonucleotide in combination with primer extension and exonuclease degradation to generate hemizygous DNA targets. Yet other methods are single molecule dilution (SMD) as described in Ruano et al., Proc. Natl. Acad. Sci. 87:6296–6300, 1990; and allele specific PCR (Ruano et al., 17 Nucleic Acids. Res. 8392, 1989; Ruano et al., 19 Nucleic Acids Res. 6877–6882, 1991; Michalatos-Beloin et al., 24 Nucleic Acids Res. 4841–4843, 1996).

In another embodiment of the haplotyping method, a $\beta_2$AR haplotype pair is determined for an individual by identifying the nucleotide at the 5'LC PS and one or more $\beta_2$AR polymorphic sites. Preferably, the additional polymorphic site(s) is selected from the group consisting of −20 PS, +46 PS, +79 PS, +100 PS and +491 PS in both copies of the $\beta_2$AR gene present in the individual. In a particularly preferred embodiment, the haplotyping method comprises identifying the nucleotide at each of the 5'LC PS, −20 PS, +46 PS, +79 PS, +100 PS and +491 PS in both copies of the $\beta_2$AR gene present in the individual. When haplotyping both copies, the identifying step is preferably performed using first and second polynucleotides comprising each copy placed in separate containers. However, it is also envisioned that if the first and second polynucleotides are labeled with different tags, or are otherwise separately distinguishable or identifiable, it could be possible in some cases to perform the method in the same container. For example, if first and second polynucleotides are labeled with different first and second fluorescent dyes, respectively, and an allele-specific oligonucleotide labeled with yet a third different fluorescent dye is used to assay the polymorphic site(s), then detecting a combination of the first and third dyes would identify the polymorphism in the first polynucleotide while detecting a combination of the second and third dyes would identify the polymorphism in the second polynucleotide.

As described above and in the Examples below, the 5'LC thymine allele exhibits linkage disequilibrium with the coding block polymorphisms encoding the Arg16 and Gln27 $\beta_2$AR variants and vice versa, the 5'LC cytosine allele is linked to the coding block polymorphisms encoding the Gly16 and Glu27 $\beta_2$AR variants. This relationship is the basis for another embodiment of the invention, which is a method for predicting an individual's genotype at one or both of +46 PS and +79 PS. The method comprises determining the individual's genotype at the 5'LC PS and assigning a genotype for one or both of +46 PS and +79 PS that is consistent with the 5'LC genotype. If the 5'LC genotype is homozygous T, the genotype at +46 PS is probably homozygous A and the genotype at +79 PS is probably homozygous C, while conversely, if the 5'LC genotype is homozygous C, the genotype at +46 PS is probably homozygous G and the genotype at +79P S is probably homozygous G.

It is also contemplated that the above genotyping and haplotyping methods of the invention may be performed in combination with identifying the genotype(s) and/or haplotype(s) for other genomic regions.

In the genotyping and haplotyping methods of the invention, the identity of a nucleotide (or nucleotide pair) at a polymorphic site may be determined by amplifying a target region(s) containing the polymorphic site(s) directly from one or both copies of the $\beta_2$AR gene present in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

Since an MspAII restriction site is lost when the T allele is present at the 5'LC PS, the identity of the nucleotide at the 5'LC PS may also be determined by digesting an amplified target region containing this site with MspAII and then analyzing the reaction products by standard size separation techniques such as agarose or polyacrylamide gel electrophoresis. The presence or absence of the enzyme restriction site as determined by this MspAII restriction fragment length polymorphism (RFLP) analyses is used to determine whether the individual being tested is homozygous for the C allele or T allele, respectively. The presence of both undigested and digested reaction products indicates the individual is heterozygous C/T at the 5 LC polymorphic site. In a preferred embodiment, the forward and reverse primers used to amplify the target region comprise the following sequences 5'-GCTGAATGAGGCTTCCAGGC-3' (SEQ ID NO:13) and 5'-CGCATGGCTTCTATTGGGTG-3'(SEQ ID NO:14), respectively.

The target region(s) may be amplified using any oligonucleotide-directed amplification method, including but not limited to polymerase chain reaction (PCR) (U.S. Pat. No. 4,965,188), ligase chain reaction (LCR) (Barany et al., *Proc. Natl. Acad. Sci. USA* 88:189–193, 1991; WO9/01069), and oligonucleotide ligation assay (OLA) (Landegren et al., *Science* 241:1077–1080, 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89!06700) and isothermal methods (Walker et L., *Proc. Natl. Acad. Sci. USA* 89:392–396,1992.

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C., and more preferably within 2° C., of each other when hybridizing to each of the polymorphic sites being detected.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype or haplotype for one or more polymorphic sites in the $\beta_2$AR gene of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., *Proc. Natl. Acad. Sci. USA* 82:7575, 1985; Meyers et al., *Science* 230:1242, 1985) and proteins which recognize nucleotide mismatches, such as the *E. coli* mutS protein (Modrich, P. *Ann. Rev. Genet.* 25:229–253 (1991). Alternatively, variant alleles can be identified by single strand conformation polymorphism (SSCP) analysis (Orita et al., *Genomics* 5:874879, 1989; Humphries et al., in *Molecular Diagnosis of Genetic Diseases*, R. Elles, ed., pp 321–340, 1996) or denaturing gradient gel electrophoresis (DGGE) (Wartell et al., *Nucl. Acids Res.* 18:2699–2706, 1990; Sheffield et al., *Proc. Natl. Acad. Sci. USA* 86:232–236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524. Related methods are disclosed in WO91/02087, WO90/09455, WO95/17676, and U.S. Pat. No. 5,302,509. Another such method is allele-specific PCR (Ruano et al., *Nucl. Acids Res.* 17:8392, 1989; Ruano et al., *Nucl Acids Res.* 19, 6877–6882, 1991; WO 93/22456; Turki et al.,*J. Clin. Invest.* 95:1635–16A1, 1995). In addition, multiple polymorphic sites may be investigated by simultaneously amplifying multiple regions of the nucleic acid using sets of allele-specific primers as described in Wallace et al. (WO89/10414).

Another aspect of the invention relates to detecting which variant(s) of the 5'LC peptide is expressed in an individual. In one embodiment, a biological sample from the individual is contacted with a first antibody that is specifically immunoreactive with only one of the 5'LC peptide variants and the formation of a complex with the first antibody is detected. In a preferred embodiment, the method also comprises contacting the biological sample with a second antibody that is specifically immunoreactive with the other 5'LC peptide variant and the formation of a complex with the second antibody is detected. Complex formation with both first and second antibodies indicate the individual is heterozygous at the $\beta_2$AR 5'LC polymorphic site.

Suitable immunoassays for use in this detection method include radioimmunoassay, Western blot assay, immunofluorescent assay, enzyme linked immunoassay (ELISA), chemiluminescent assay, immunohistochemical assay, immunocytochemical assay, and the like (see, e.g., *Principles and Practice of Immunoassay*, 1991, Eds. Christopher P. Price and David J. Neoman, Stockton Press, New York, N.Y.; *Current Protocols in Molecular Biology,* 1987, Eds. Ausubel et al., John Wiley and Sons, New York, N.Y.). Standard techniques known in the art for ELISA are described in *Methods in Immunodiagnosis,* 2nd Ed., Eds. Rose and Bigazzi, John Wiley and Sons, New York 1980; and Campbell et al., 1984, *Methods in Immunology,* W. A. Benjamin, Inc.). Such assays may be direct, indirect, competitive, or noncompetitive as described in the art (see, e.g., *Principles and Practice of Immunoassay,* 1991, Eds. Christopher P. Price and David J. Neoman, Stockton Pres, NY, N.Y.; and Oellirich, M., 1984, *J. Clin. Chem. Clin. Biochem.,* 22:895–904). Proteins may be isolated from test specimens and biological samples by conventional methods, as described in *Current Protocols in Molecular Biology, supra.*

Exemplary antibody molecules for detecting $\beta_2$AR 5'LC peptide variants are intact immunoglobulin molecules, substantially intact immunoglobulin molecules, or those portions of immunoglobulin molecules that contain the antigen binding site. Polyclonal or monoclonal antibodies may be produced by methods conventionally known in the art (e.g., Kohler and Milstein, 1975, *Nature,* 256:495–497; Campbell "Monoclonal Antibody Technology, the Production and Characterization of Rodent and Human Hybridomas", 1985, In: "Laboratory Techniques in Biochemistry and Molecular Biology," Eds. Burdon et al., Volume 13, Elsevier Science Publishers, Amsterdam). The antibodies or antigen binding fragments thereof may also be produced by genetic engineering. The technology for expression of both heavy and light chain genes in *E. coli* is the subject of PCT patent applications, publication number WO 90/443, WO 90/443 and WO 90/4424 and in Huse et al., 1989, *Science,* 246:1275–1281. The antibodies may also be humanized (e.g., Queen, C. et al. 1989 *Proc. Natl. Acad. Sci.* 86;10029).

The above described genotyping methods are useful in methods for determining the frequency of a $\beta_2$AR genotype or haplotype in a population. The method comprises determining the genotype or the haplotype pair for the $\beta_2$AR 5' gene that is present in each member of the population and calculating the frequency any particular $\beta_2$AR genotype or haplotype is found in the population. In a preferred embodiment, the $\beta_2$AR genotype may also comprise the nucleotide pair(s) detected at one or more additional $\beta_2$AR polymorphic sites. The population may be a reference population, a family population, a same sex population, a population group, a trait population (e.g., a group of individuals exhibiting a trait of interest such as a medical condition or response to a therapeutic treatment).

Frequency data for such $\beta_2$AR genotypes or haplotypes in reference and trait populations are useful for identifying an association between a trait and a $\beta_2$AR 5'LC polymorphism, a $\beta_2$AR genotype or a $\beta_2$AR haplotype. The trait may be any detectable phenotype, including but not limited to genetic predisposition to a disease or response to a treatment. The method comprises obtaining data on the frequency of the $\beta_2$AR 5'LC polymorphism, $\beta_2$AR genotype or $\beta_2$AR haplotype of interest in a reference population as well as in a population exhibiting the trait. Frequency data for one or both of the reference and trait populations may be obtained by genotyping or haplotyping each individual in the populations using one of the methods described above. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the 5'LC polymorphism, $\beta_2$AR genotype or $\beta_2$AR haplotype of interest are compared in the reference and trait populations. If a 5'LC polymorphism, $\beta_2$AR genotype or $\beta_2$AR haplotype is more frequent in the trait population plan in the reference population to a statistically significant degree, then the trait is predicted to be associated with that 5'LC polymorphism, $\beta_2$AR genotype or $\beta_2$AR haplotype.

In a preferred embodiment of the method, the trait of interest is a clinical response exhibited by a patient to some therapeutic treatment, for example, response to a drug targeting $\beta_2$AR or response to a therapeutic treatment for a medical condition. As used herein, "medical condition" includes but is not limited to any condition or disease manifested as one or more physical and/or psychological symptoms for which treatment is desirable, and includes previously and newly identified diseases and other disorders. As used herein the term "clinical response" means any or all of the following: a quantitative measure of the response, no response, and adverse response (i.e, side effects).

In order to deduce a correlation between a clinical response to a treatment and a 5'LC polymorphism, $\beta_2$AR genotype or $\beta_2$AR haplotype, it is necessary to obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been assessed for the clinical characteristics of the medical condition of interest. Such clinical characteristics may include symptoms, disease severity, response to therapy and the like. This characterization is important in cases where the symptom(s) being presented by the patients can be caused by more than one underlying condition, and where treatment of the underlying conditions are not the same. An example of this would be where patients experience breathing difficulties that are due to either asthma or respiratory infections. If both sets were treated with an asthma medication, there would be a spurious group of apparent non-responders that did not actually have asthma. These people would affect the ability to detect any correlation between haplotype and treatment outcome. Characterization of potential patients could employ a standard physical exam or one or more lab tests.

The therapeutic treatment of interest is administered to each individual in the trial population and each individual's response to the treatment is measured using one or more predetermined criteria. It is contemplated that in many cases, the trial population will exhibit a range of responses and that the investigator will choose the number of responder groups (e.g., none, low, medium, high) made up by the various responses. In addition, the $\beta_2$AR gene for each individual in the trial population is genotyped at least at the 5'LC polymorphic site, which may be done before or after administering the treatment.

After both the clinical and polymorphism data have been obtained, correlations are created between individual response and the presence of a $\beta_2$AR 5'LC polymorphism, $\beta_2$AR genotype or $\beta_2$AR haplotype. Correlations may be produced in several ways. In one embodiment, individuals are grouped by their $\beta_2$AR genotype or $\beta_2$AR haplotype and then the averages and standard deviations of clinical responses exhibited by the members of each group are calculated. These results are then analyzed to determine if any observed variation in clinical response between genotype or haplotype groups is statistically significant. Another method involves categorizing the response (e.g., none, low, medium, high or other such grades) and then assessing whether a particular genotype is more common in one group of responders compared to another. Statistical analysis methods which may be used are described in L. D. Fisher and G. vanBelle, "Biostatistics: A Methodology for the Health Sciences", Wiley-Interscience (New York) 1993.

It is also contemplated that the above methods for identifying associations between a $\beta_2AR$ 5'LC polymorphism, or $\beta_2$ genotypes and haplotypes containing the $\beta_2AR$ polymorphism, may be performed in combination with genotype(s) and haplotype(s) for one or more additional genomic regions.

The above described genotyping and haplotyping methods are also useful for predicting an individual's predisposition to various diseases modified by the $\beta_2AR$. At the time the present invention was made, it was well-known in the medical arts that the $\beta_2AR$ is expressed in a number of tissues in the human body and that the amount of such expression modifies a number of diseases and physiologic processes. As an example, when activated by an agonist (or to a lesser extent by the endogenous agonist epinephrine), the $\beta_2AR$ relax airway smooth muscle and open the constricted airways during an asthma attack. It follows, then, that a polymorphism that causes, for example, the $\beta_2A$ to be minimally expressed in the lung would result in worse asthma (i.e., endogenous epinephrine doesn't work as well). The same logic is applied to $\beta_2AR$ expressed in other organs/cells in the body, with the predictable consequences of a low or high expression level due to a polymorphism. Thus, an altered level of expression would be a risk factor for a disease or cause a more severe form of the indicated diseases in the right-hand column of Table 1.

TABLE 1

Location and Function of $\beta_2$-adrenergic receptors in humans*

| Location | Function | Disease Modifying |
|---|---|---|
| Heart | Increase rate<br>Increase contractility | Congestive Heart Failure<br>Arrhythmia<br>Ischemic Heart Disease |
| Arterioles | Dilatation | Hypertension<br>Migraine |
| Veins | Dilatation | Hypertension |
| Lungs<br>(tracheal & bronchial<br>smooth muscle) | Relaxation | Asthma<br>COPD<br>Anaphylaxis |
| Fat cells | Lipolysis | Obesity |
| Pancreas (islets) | Insulin secretion | Diabetes |
| Skeletal muscle | Glycogen breakdown | Diabetes |
| Uterus | Relaxation | Premature labor |

*Adapted from Goodman and Gilman's The Pharmacological Basis of Therapeutics, Pergamon Press, 1990, New York, pp 89–90.

A brief explanation of the expected effects of the P2AR 5' LC polymorphisms for each disease in Table 1 follows.

Congestive heart failure—In this syndrome the heart has decreased cardiac output which can be increased by activating $\beta_2AR$ which increase heart rate and the force of contraction. Thus, individuals homozygous for the C polymorphism at the $\beta_2AR$ 5' LC PS would have an increased risk for decompensation.

Ischemic Heart Disease—Individuals suffering from this condition have blocked coronary arteries and thus a limited capacity to tolerate increased cardiac demand. Thus, an increased cardiac output caused by increased levels of $\beta_2AR$ can lead to myocardial infarction in these patients. The skilled artisan would expect, therefore, that individuals suffering from ischemic heart disease who are homozygous for the $\beta_2AR$ 5'LC T polymorphism, which leads to higher levels of $\beta_2AR$ expression than the C allele, are at an increased risk of having a myocardial infarction.

Cardiac arrhythmias—Activated $\beta_2AR$ cause an increase in heart rate which predisposes certain individuals with conduction system defects to arrhythmias. Thus, the higher $\beta_2AR$ expression expected in individuals homozygous for T at the 5'LC polymorphic site would be a risk factor for arrhythmias.

Hypertension —Blood pressure is regulated, in part, by systemic vascular resistance which is due to contraction of the smooth muscle surrounding the small resistance arteries known as arterioles. $\beta_2AR$ are expressed on this muscle and thus activation relaxes it and lowers resistance and blood pressure. Because polymorphisms leading to lower expression would predispose to hypertension, an individual homozygous for C at the 5'LC PS would have an increased risk for developing hypertension.

Vascular disease—Diseases where vascular flow is compromised to a given organ, due to atherosclerosis or abnormal neurogenic control of tone, such as migraine, are amenable to treatment with vasodilators or vasoconstrictors. As discussed above, arterioles alter resistance and flow and are relaxed (opened) by $\beta_2AR$. Thus, patients homozygous for the C polymorphism in the $\beta_2AR$ 5'LC, which causes decreased $\beta_2AR$ expression, would be at increased risk for a more severe form of obstructive or neurogenic vascular disease. Individuals homozygous for the T polymorphism would be expected to be at increased risk of migraine headaches since they are genetically predisposed to cerebral vasodilation.

Asthma, COPD, anaphylaxis—The airways have smooth muscle which when contracted leads to obstruction of airflow, termed bronchospasm, in asthma, COPD (a syndrome with varying features of emphysema and chronic bronchitis), and anaphylaxis. $\beta_2AR$ on airway smooth muscle relax the muscle and open the airways. Therefore, patients homozygous for the C polymorphism in the $\beta_2AR$ 5'LC would be predisposed to bronchospasm.

Obesity—Fat cells express three PAR subtypes, including the $\beta_2$ Activation of the $\beta_2AR$ causes breakdown of fat in the cells. Thus, at the time the invention was made, the skilled artisan would have expected that a polymorphism causing reduced $\beta_2AR$ expression would be a risk factor for developing obesity since a lower efficiency of lipolysis in fat cells would be expected in individuals carrying this polymorphism. This expectation was recently confirmed by a clinical study, which demonstrated that the 5' LC C polymorphism is indeed associated with obesity (29).

Diabetes—In diabetes, a decrease in insulin (or a resistance to insulin's action) causes elevated glucose levels in the blood. The islet cells of the pancreas are responsible for insulin secretion, and these cells express $\beta_2AR$, which act to increase insulin secretions. At the time the invention was made, the skilled artisan would have expected that a polymorphism that causes decreased $\beta_2AR$ expression would result in lower insulin secretion and predispose to diabetes. Skeletal muscle glycogen metabolism is also altered by $\beta_2AR$ activation, and a complex interplay with insulin secretion and lipolysis (see above) can further the potential for the diabetic state. Of note, this prediction is supported by the results of a recent clinical study, which found significant association between the 5' LC C polymorphism and Type 2 diabetes (29).

Premature labor—The uterine muscle expresses $\beta_2$AR which serve to relax the muscle. $\beta_2$AR agonists such as ritodrine are administered to inhibit contractions of the uterus when premature labor develops. Patients with a polymorphism that results in decreased $\beta_2$AR expression would be predisposed to higher uterine muscle tone and at higher risk for early labor.

An individual's predisposition to these diseases can be predicted by determining the individual's genotype for the $\beta_2$AR 5'LC polymorphic site. Although nucleic acid isolated from any tissue from the individual may be used for genotyping, the typical genotyping procedure comprises drawing a patient's blood and extracting genomic DNA from the cells of the blood (e.g., peripheral blood mononuclear cells, leukocytes, or lymphocytes). In addition, if necessary and prudent, prenatal diagnosis can be accomplished by testing fetal cells or amniotic fluid. The identity of the nucleotide or nucleotide pair at the $\beta_2$AR 5'LC polymorphic site can be determined by any of the means described herein.

As described in the Examples below, the inventor herein has discovered that asthmatic patients who are homozygous T at the 5'LC polymorphic site are less likely to exhibit a bronchodilating response to the $\beta$-agonist albuterol than asthmatic patients having other 5'LC genotypes. Thus, the invention also provides a method for predicting a patient's bronchodilating response to a $\beta_2$-agonist which comprises determining the patient's genotype for the 5'LC PS. A patient who is homozygous T at this site is unlikely to exhibit a bronchodilating response to the $\beta_2$-agonist while a patient who is homozygous C or heterozygous C/T at this site is likely to exhibit a bronchodilating response to the $\beta_2$-agonist. As used herein, the term "bronchodilating response" means an increase of greater than 12% in the forced expiratory flow between 25% and 75% of the forced vital capacity ($FEF_{25-75}$) after administration of the standard dose of the $\beta_2$-agonist. Based on the patient's genotype for the $\beta_2$AR 5'LC PS, the physician can determine whether the patient should be treated with higher doses of the $\beta_2$-agonist, or with an alternative therapy. In a preferred embodiment of this method, the $\beta_2$-agonist is albuterol.

EXAMPLES

The Examples herein are meant to exemplify the various aspects of carrying out the invention and are not intended to limit the scope of the invention in any way. The Examples do not include detailed descriptions for conventional methods employed, such as in the synthesis of oligonucleotides or preparation of antibodies. Such methods are well known to those skilled in the art and are described in numerous publication's, for example, Sambrook, Fritsch, and Maniatis, *Molecular Cloning: a Laboratory Manual, 2nd Edition*, Cold Spring Harbor Laboratory Press, USA, (1989).

Example 1

This example illustrates the detection of a polymorphic site in the 5' leader cistron of the $\beta_2$AR gene. The study was approved by the University of Cincinnati College of Medicine Institutional Review Board. Genomic DNA was derived by the cetylmethyl ammonium bromide method (15) from peripheral blood obtained from 176 healthy Caucasian subjects without histories of chronic disease.

The first nucleotide of the initiator methionine codon of the $\beta_2$AR coding block is denoted as nucleotide 1 and the adjacent 5' residue as nucleotide −1. The 5' leader cistron is thus localized to nucleotides −102 to −42 (nucleotides 1487–1546 of FIG. 1). A polymerase chain reaction was carried out using primers that provided for an amplification product spanning this region (sense: 5'-AAGGACACCACCTCCAGCTTTAG-3', (SEQ ID NO:11); antisense: 5'-CGCATGGCTTCTATTGGGTG-3' (SEQ ID NO:12). Each reaction contained 1 U of Amplitaq polymerase (Perkin Elmer), 500 ng genomic DNA 250 $\mu$M of each dNTP, and 37.5 pmol of each primer in a final volume of 50 $\mu$l. After an initial denaturation step of 98° C. for 2 minutes, 35 cycles of 98° C. for 30 sec, 56° C. for 30 see, and 72° C. for 30 sec were carried out, followed by a 7-minute final extension at 72° C. Ten $\mu$l of the PCR reaction was electrophoresed on a 1% agarose gel and visualized by ethidium bromide staining. The remaining PCR product was purified with a commercial kit (Promega) and was sequenced by an automated sequencer (ABI 377 Prism) using dye-terminator chemistry (FIG. 4A). After sequencing 46 individuals, a single polymorphism of C or T at position −47, which corresponds to nucleotide 55 of the leader cistron ORF (nucleotide 1541 of FIG. 1), was identified. This polymorphic site in the 5'LC results in the encoded residue at amino acid 19 being either Arg or Cys.

Figure 4B:
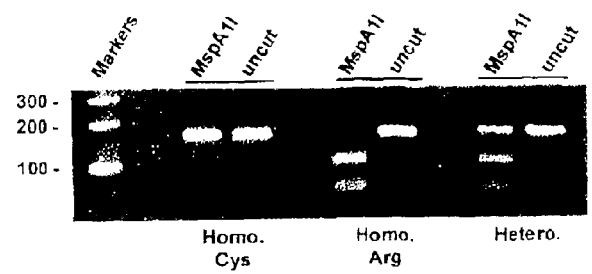

A rapid detection method was subsequently developed based on the loss of an MspaII restriction endonuclease site when T is present (FIG. 4B). In this method, a target region defined by forward primer 5'-GCTGAATGAGGCTTCCAGGC-3' (SEQ ID NO:13) and reverse primer 5'-CGCATGGCTTCTATTGGGTG-3' (SEQ ID NO:14).

As shown in Table 2 below, 13% of the 176 normal, unrelated subjects in this study were homozygous for the C (Arg19) allele and 39% were homozygous for the T (Cys19) allele, with the remainder being heterozygotes.

TABLE 2

Distribution of polymorphisms at position 19 of the 5'LC peptide.

| Genotype | No. | % |
|---|---|---|
| Homozygous Arg | 23 | 13 |
| Heterozygous | 85 | 48 |
| Homozygous Cys | 68 | 39 |

Thus, the allele frequencies were 0.37 for Arg and 0.63 for Cys in this population. The number of homozygous and heterozygous alleles that were found is in agreement with that predicted by the Hardy-Weinberg relationship (p=0.98).

Example 2

This example illustrates the effect of the $\beta_2$AR 5'LC polymorphisms on $\beta_2$AR if expression.

To test whether variation in the 5'LC altered receptor expression, cells were transiently transfected with two receptor constructs. These consisted of a contiguous stretch of 1989 bp exactly as found in the human gene, comprising a 93 bp region upstream of the leader cistron, the leader cistron with its stop codon, an additional intervening 41 bp of 5' sequence, the 2 coding sequence and 557 bp of 3' untranslated region. This cDNA was subcloned into the expression vector pBC12B1 at the BamHI site. The two constructs, denoted 5'LC-Arg19 and 5'LC-Cys19, differed only by the nucleotide at position −47. Of note, both constructs encoded for Gly at position 16 and Glu at position 27 in the $\beta_2$AR coding block, which is the most common $\beta_2$AR genotype. COS-7 cells were transfected by a DEA-Dextran method with 15 $\mu$g of either construct as previously described (17). Cells were maintained in Dulbecco's Modified Eagles medium in 10% fetal calf serum at 37° C. in a 95% air, 5% $CO_2$ atmosphere.

Two days after transfection, the confluent cells were harvested for determination of receptor expression by radioligand binding with [$^{125}$I]cyanopindolol ([$^{125}$I]CYP) using 1 μM propranolol to define non-specific binding. Cells were disrupted by scraping with a rubber policeman in cold 5 mM Tris, 2 mM EDTA, pH 7.4 buffer and the particulates centrifuged at 40,000×g for 10 minutes and resuspended in 75 mM Tris, 12 mM MgCl$_2$, 2 mM EDTA, pH 7.4 buffer. Membranes (~10 μg) were incubated in triplicate with a saturating concentration of [$^{125}$I]CYP (400 pM) without or with propranolol in the aforementioned buffer for 2 hrs at 25° C. The reaction was stopped by dilution and rapid vacuum filtration over Watman GF/C filters. Radioactivity was measured in a gamma counter at 80% efficiency. Protein was quantitated by the copper bicinchoninic method (19).

Figure 5B:
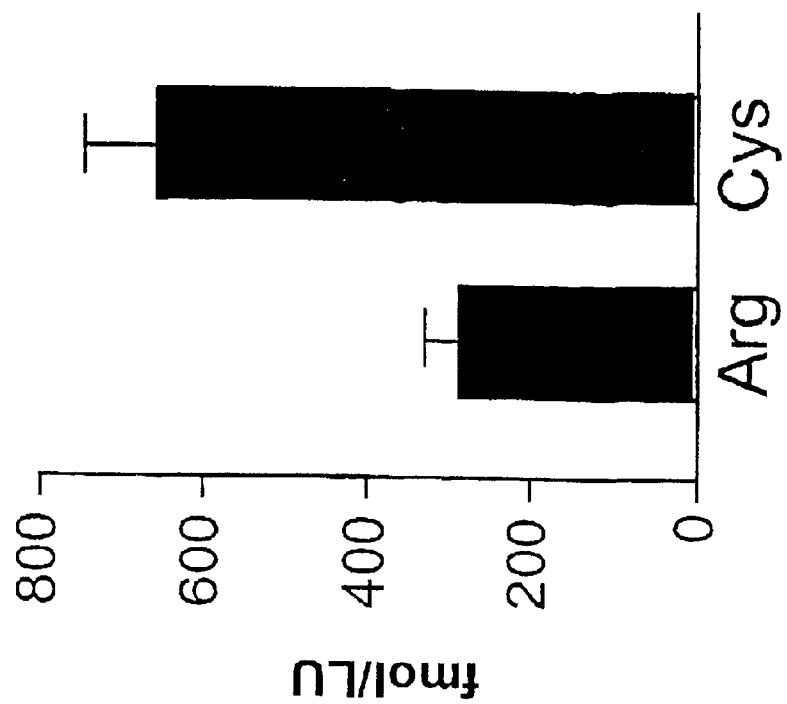
FIG. 5B shows a graph of β₂AR expression in cells co-transfected with one of the above 5'LC constructs and a construct encoding firefly luciferase, with β₂AR expression presented as fmol receptor/light unit receptor.
Figure 5A:
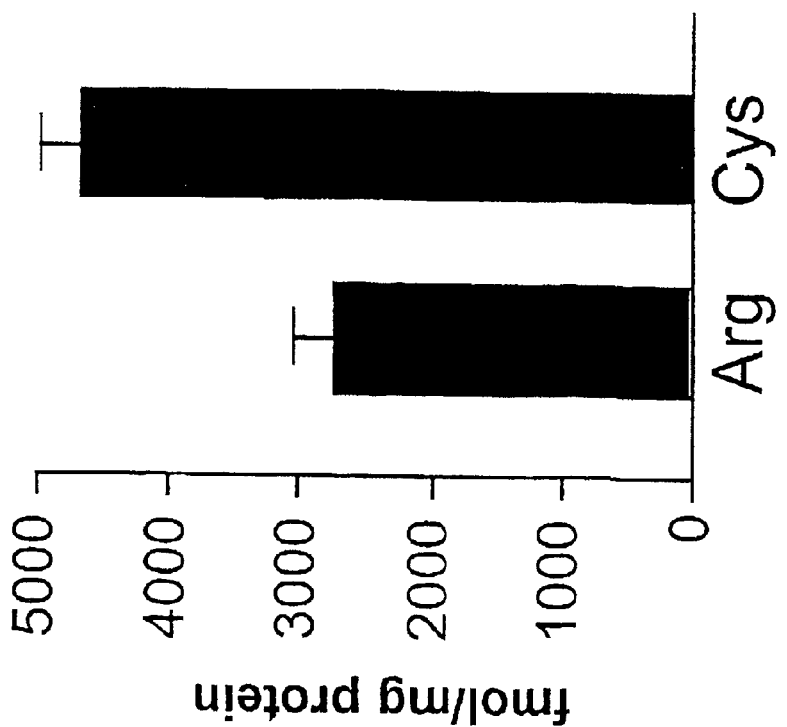
FIG. 5A shows a graph of the level of β₂AR expression in COS-7 cells transfected with one of the 5'LC-Arg 19 or the 5'LC-Cys19 constructs described in the Examples with β₂AR levels determined by radioligand binding with [$^{125}$I] CYP performed in triplicate and presented as fmol receptor/mg membrane protein.

As shown in FIG. 5A, the 5'LC-Cys19 construct resulted in 72% higher levels of expression over that obtained with the 5'LC-Arg19 construct (4666±302 vs 2711±294 fmol/mg, P<0.01). This is consistent with the aforementioned studies (14), which showed that the Arg 5'LC peptide inhibited $\beta_2$AR translation.

To control for any possible differences in transfection efficiency in the two plates, additional studies were carried out using cells co-transfected with the above constructs and a luciferase expression vector driven by the human β-actin promoter to provide for transient expression of firefly luciferase. Cells from one half of a 150 mm culture dish were scraped and used for membrane preparations as described above. Lysates prepared from the remaining cells were then assayed for luciferase expression using a commercial luciferase assay system (Promega). Luminescence was measured using a Monolight 2010 luminometer (Analytical Luminescence Laboratory) and expressed per mg of protein in the lysate. To account for differences in transfection efficiency, the value for [$^{125}$I]CYP binding (fmo/mg protein) was divided by the value for luciferase expression (light units/mg protein). The corrected value is thus reported as fmol/light unit (fmol/LU). Again, as shown in FIG. 5B, the 5'LC-Cys19 construct provided for higher $\beta_2$AR expression (130% increase) as compared to the Arg construct (656±90 vs 288±45 fmol/LU, n=4, P<0.01). Finally, adenylyl cyclase activities were determined in membranes from cells transfected with the two constructs. Consistent with the enhanced expression, isoproterenol stimulated activities were higher in membranes obtained from transfection with the 5'LC-Cys19 construct as compared to the 5'LC-Arg19 construct (66.2±4.5 vs 49.7±4.9 pmol/min/mg, P<0.02, n=5 experiments).

Assuming that the degree of DNA transfection was indeed the same between the two constructs, and the difference in $\beta_2$AR cellular expression was due to differences in peptide mediated inhibition of translation (rather than transcription or mRNA stability), then there should be no differences in $\beta_2$AR mRNA levels between cells transfected with one construct versus the other. To assess this, mRNA levels were determined by a quantitative ribonuclease protection assay which included a probe for β-actin as a control.

Figure 6:
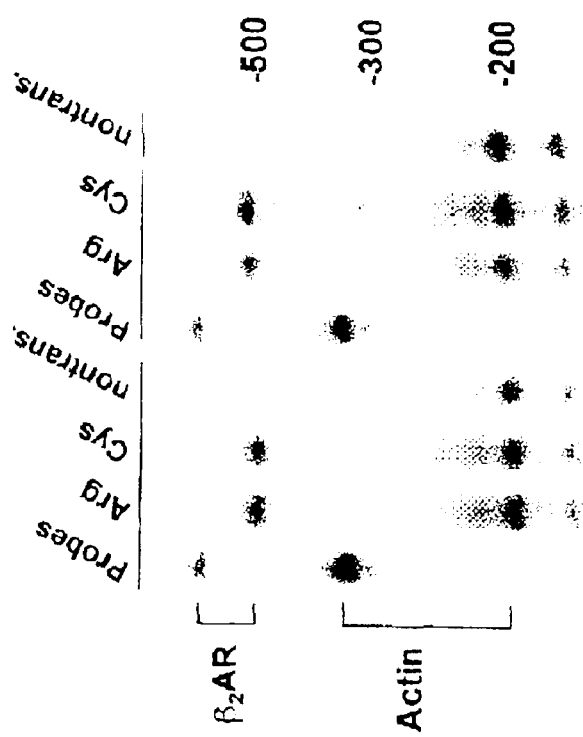
FIG. 6 illustrates the results of ribonuclease protection assays, which identify levels of β₂AR mRNA and actin mRNA in COS-7 cells transfected with one of the above 5'LC constructs.

Total cellular RNA was prepared from transfected cells by an acid guanidinium thiocyanate-phenol-chloroform extraction reagent (Molecular Research, Cincinnati, Ohio) and $\beta_2$AR transcripts delineated by ribonuclease protection assays (RPA) in a manner similar to that previously described (18). A template for the synthesis of riboprobes was prepared by subcloning a cDNA encoding the $\beta_2$AR ORF into the HindIII/XbaI sites of plasmid pSP72 (Promega). Plasmid linearized with EcoNI was then used for in vitro transcription reactions with T7 polymerase and [$^{32}$P]UTP to generate a 563 bp antisense riboprobe corresponding to the distal 500 bp of the $\beta_2$AR ORF. In addition, a radiolabeled antisense riboprobe for β-actin was generated from a commercial template (Ambion) using T7 polymerase. RPAs were performed as previously reported (18) by hybridizing 20 μg of total cellular RNA with both the actin and $\beta_2$AR riboprobes. The hybridized products were digested with RNAse A and T1, after which protected fragments were separated by electrophoresis on 6% polyacrylamide gels containing 8M urea. Radiographic bands corresponding to the protected fragments were visualized with a PhosphoImager (Molecular Dynamics) and conventional autoradiography. Band density was quantitated on the phosphorimage with the ImageQuant software package (Molecular Dynamics). To account for minor differences in sample loading and recovery, the measured value for the $\beta_2$AR protected fragment was normalized to that of m-actin in the same sample. The results of these ribonuclease protection assays are shown in FIG. 6. In four independent experiments, $\beta_2$AR mRNA levels were found to be indistinguishable between cells transfected with the two constructs (as were transcripts for β-actin).

Having shown that the 5' cistron polymorphisms had differential effects on $\beta_2$AR expression in a recombinant system, we wondered whether receptor expression correlated with the 5' leader cistron polymorphism in cells that endogenously express the $\beta_2$AR. Human airway smooth muscle was chosen because it expresses exclusively $\beta_2$AR, and the receptors on this cell have known physiologic relevance. Human airway smooth muscle cells were obtained by rapid autopsy from individuals without lung disease. These cells were established and maintained in primary culture as previously described (5), genotyped and radioligand binding carried out as described above.

Figure 7:
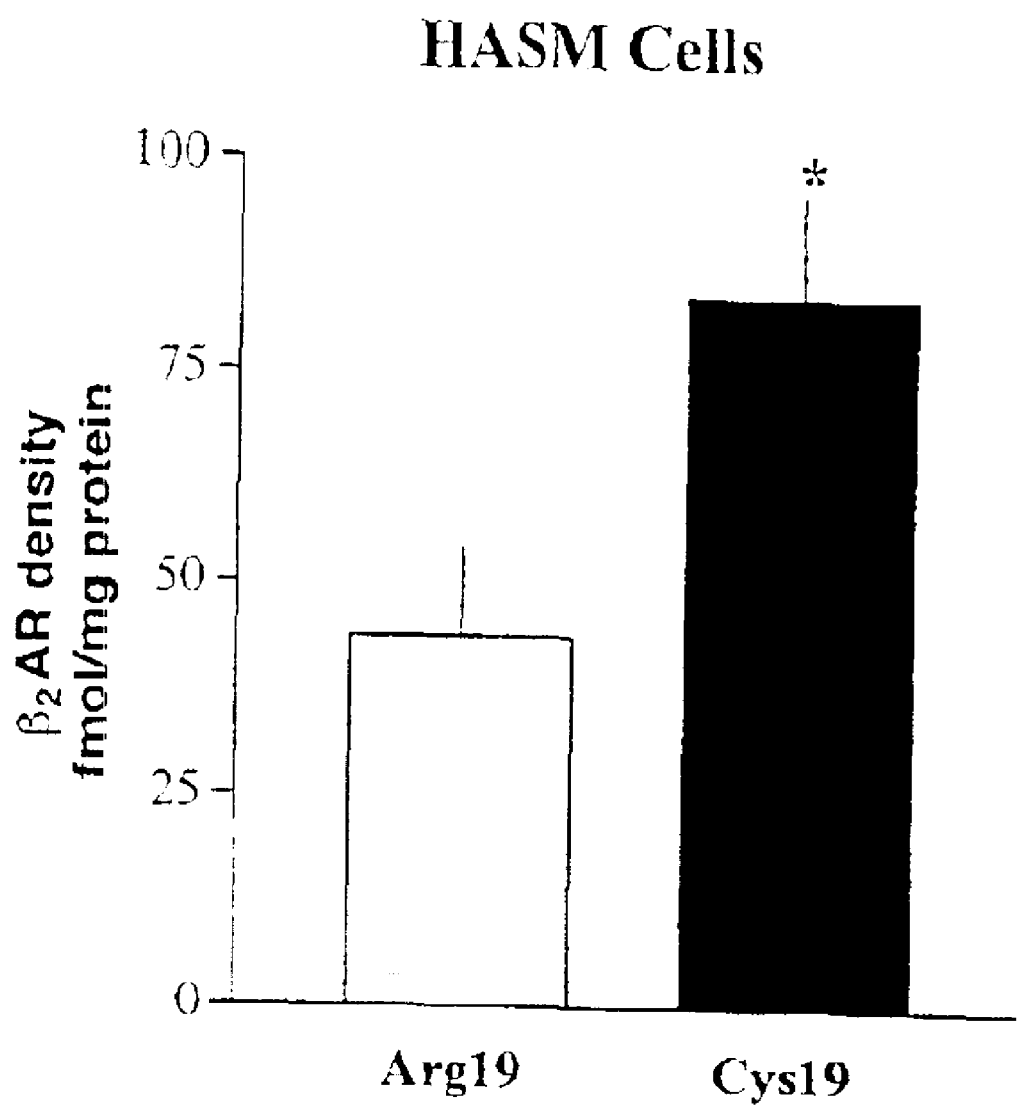
FIG. 7 shows a graph of β₂AR expression in primary cultures of human airway smooth muscle cells (HASM) homozygous for the 5'LC C allele (Arg19) or homozygous for the 5'LC T allele (Cys19).

Of note, linkage disequilibrium exists between the 5' LC and the coding block polymorphisms (see below), and a limited number of human airway smooth muscle cell lines available were homozygous for the 5' LC polymorphisms. Thus, matches at positions 16 and 27 between the two cell lines were not utilized. (The 5' LC-Arg cells were homozygous for Gly and Glu at coding positions 16 and 27, while the 5' LC-Cys cells were Arg and Gln.) Nevertheless, a clear difference in $\beta_2$AR expression was found. As shown in FIG. 7, for cells homozygous for the 5'LC-Arg19 polymorphism, [$^{125}$I]CYP binding revealed $\beta_2$AR expression of 44±10 fmol/mg. As was seen with the recombinant studies, those with the 5'LC-Cys polymorphism had higher expression levels, which amounted to 84±12 fmol/mg (n=5, P<0.02).

Example 3

This example illustrates there is linkage disequilibrium between the previously described polymorphisms at nucleotides 46 and 79 (amino acids 16 and 27 of the receptor protein) and the 5' leader cistron polymorphisms.

To assess linkage disequilibrium between these polymorphic sites, some of the normal subjects underwent genotyping at all 3 sites. The polymorphisms at nucleotides 46 and 79 in the $\beta_2$AR coding block were detected by the genetic bit analysis technique (16). For this analysis, only those subjects that were homozygous were utilized so as to unequivocally assign haplotypes. These results (shown in Table 3) show linkage disequilibrium between the Cys 5' leader cistron polymorphism and the Gln27 coding block polymorphism (P<0.0001) and to a lesser extent the Arg$_6$ coding block polymorphism. The frequencies of other genotypic combinations at these three positions are shown in Table 4.

TABLE 3

Haplotypes of $\beta_2$AR polymorphisms in the 5' cistron and the coding block*.

| | 5' leader cistron | | |
| --- | --- | --- | --- |
| Coding block | Arg19 | Cys19 | Pvalue |
| Arg16 | 0 | 19 | <0.0001 |
| Gly16 | 19 | 6 | |
| Gln27 | 0 | 42 | <0.0001 |
| Glu27 | 18 | 0 | |

*Shown are the number of subjects in each group.

TABLE 4

Genotypes at three polymorphic loci of the $\beta_2$AR gene (n = 130 subjects).*

| Genotype | | | | |
| --- | --- | --- | --- | --- |
| 5'LC19 | cb16 | cb27 | No. | % Total |
| het | het | het | 41 | 31.5 |
| het | Gly | het | 25 | 19.2 |
| Cys | Arg | Gln | 19 | 14.6 |
| Arg | Gly | Glu | 18 | 13.8 |
| Cys | het | Gln | 17 | 13.1 |
| Cys | Gly | Gln | 6 | 4.6 |
| het | het | Gln | 1 | 0.8 |
| Arg | Gly | het | 1 | 0.8 |
| Cys | het | het | 1 | 0.8 |
| het | Gly | Gln | 1 | 0.8 |

*5'LC19, $\beta_2$AR 5' leader cistron; cb, $\beta_2$AR coding block; het, heterozygous; Arg, Cys, Gln, Glu represent homozygous alleles at these positions.

Example 4

This example illustrates there is an association between TT genotype at the $\beta_2$AR 5'LC polymorphic site and lack of response to albuterol.

For this study, 134 patients with asthma were enrolled to determine whether either of the polymorphisms at nucleic acid −47 in the $\beta_2$AR gene alter the bronchodilating response to $\beta$-agonist. The percent (%) change in the forced expiratory flow between 25% and 75% of the forced vital capacity ($FEF_{25-75}$) was used as a measure of responsiveness. Patients underwent pulmonary function testing to measure $FEF_{25-75}$ and then received 2 puffs (total of 180 micrograms) of aerosolized albuterol by metered dose inhaler. Thirty minutes later the $FEF_{25-75}$ measurement was repeated. Based on accepted national standards, an increase in $FEF_{25-75}$ of greater than 12% was considered a response, while 12% or less was considered no response.

Figure 8:
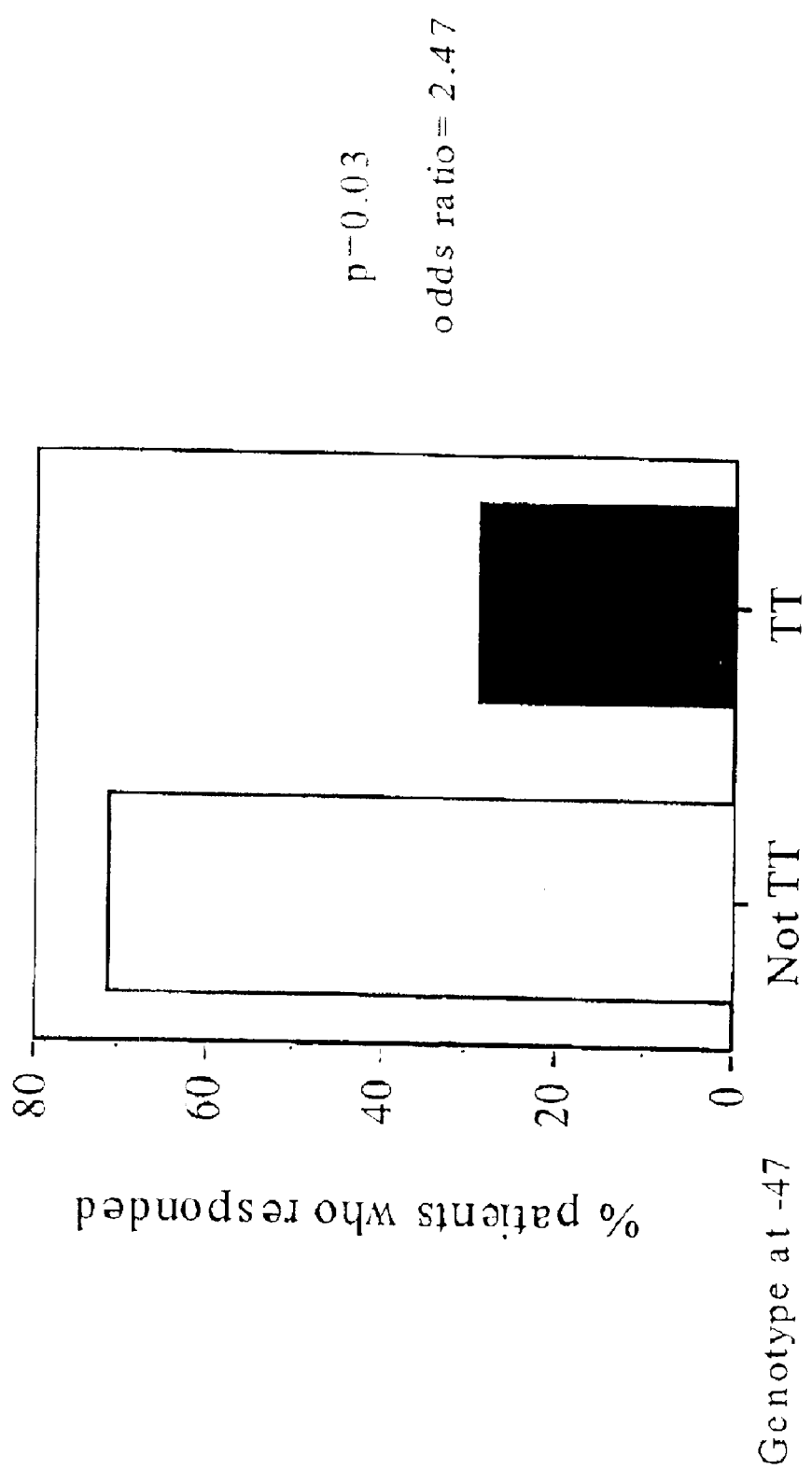
FIG. 8 shows a graph relating genotype for the 5'LC polymorphic site and the percent of patients who responded to the β-agonist albuterol.

As shown in FIG. 8, there was a clear difference in the number of responders depending on genotype. Only 28.8% of patients with the TT genotype at the 5'LC PS exhibited a bronchodilating response to albuterol, while 71.1% of those without this genotype (TC or CC) had a response. The p value for this comparison by Chi-square analysis was p=0.03, which is statistically significant based on customary standards that p values less than 0.05 represent statistical significance. In addition, the odds ratio for having no response to albuterol if a patient had the TT genotype is 2.47. These results were not confounded by the severity of the asthma or whether the patient had allergic or non-allergic asthma. Thus, it is believed the TT genotype for the 5'LC PS is a specific marker for lack of responsiveness to albuterol. Conversely, the CC genotype and C/T genotype are markers for responsiveness to albuterol.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated in their entirety by reference. The discussion of references herein is intended merely to summarize the assertions made by their authors and no admission is made that any reference constitutes prior art. Applicants reserve the right to challenge the accuracy and pertinency of the cited references.

References

1. Reihsaus, E., M. Innis, N. MacIntyre, and S. B. Liggett. 1993. Mutations in the gene encoding for the $\beta_2$-adrenergic receptor in normal and asthmatic subjects. *Am J Resp Cell Mol Biol* 8:334–339.
2. Liggett, S. B. 1995. Functionalpropertiesofhuman $\beta_2$-adrenergic receptor polymorphisms. News in Physiologic Sciences 10:265–273.
3. Green, S., J. Turki, M. Innis, and S. B. Liggett. 1994. Amino-terminal polymorphisms of the human $\beta_2$-adrenergic receptor impart distinct agonist-promoted regulatory properties. *Biochem* 33:9414–9419.
4. Green, S. A., G. Cole, M. Jacinto, M. Innis, and S. B. Liggett. 1993. A polymorphism of the human $\beta_2$-adrenergic receptor within the fourth transmembrane domain alters ligand binding and functional properties of the receptor. *J Biol Chem* 268:23116–23121.
5. Green, S. A., J. Turki, P. Bejarano, I. P. Hall, and S. B. Liggett. 1995. Influence of $\beta_2$-adrenergic receptor genotypes on signal transduction in human airway smooth muscle cells. *Am J Resp Cell Mol Biol* 13 :25–33.
6. Liggett, S. B. 1996. The genetics of $\beta_2$-adrenergic receptor polymorphisms: relevance to receptor function and asthmatic phenotypes. In The Genetics of Asthma. S. B. Liggett and D. A. Meyers, editors. Marcel Dekker, New York. 455–478.
7. Turki, 3., J. Pak, S. Green, R. Martin, and S. B. Liggett. 1995. Genetic polymorphisms of the $\beta_2$-adrenergic receptor in nocturnal and non-nocturnal asthma: evidence that Gly16 correlates with the nocturnal phenotype. *J Clin Invest* 95:1635–1641.
8. Hall, I. P., A. Wheatley, P. Wilding, and S. B. Liggett. 1995. Association of the Glu27 $\beta_2$-adrenoceptor polymorphism with lower airway reactivity in asthmatic subjects. *Lancet* 345:1213–1214.
9. Martinez, F. D., P. E. Graves, M. Baldini, S. Solomon, and R. Erickson. 1997. Association between genetic polymorphisms of the beta2-adrenoceptor and response to albuterol in children with and without a history of wheezing. *J Clin Invest* 100:3184–3188.
10. Dewar, J. C., J. Wilkinson, A. Wheatley, N. S. Thomas, I. Doull, N. Morton, P. Lio, J. Harvey, S. B. Liggett, I. S. Holgate, and I. P. Hall. 1997. The glutamine 27 $\beta_2$-adrenoceptor polymorphism is associated with elevated immunoglobulin E levels in asthmatic families. *J Allergy Clin Immunol* 100:261–265.
11. Tan, S., I. P. Hall, 1. Dewar, E. Dow, and B. Lipworth. 1997. Association between beta 2-adrenoceptor polymorphism and susceptibility to bronchodilator desensitization in moderately severe stable asthmatics. *Lancet* 350:995–999.

12. Kobilka, B. K., R. A. F. Dixon, T. Frielle, H. G. Dohlman, M. A. Bolanowski, I. S. Sigal, T. L. Yang-Feng, U. Franke, M. G. Caron, and R. J. Lefkowitz. 1987. cDNA for the human, $\beta_2$-adrenergic receptor: a protein with multiple membrane spanning domains and a chromosomal location shared with PDGF receptor gene. Proc.Natl.Acad.Sci., USA 84:46–50.

13. Kobilka, B. K., T. Frielle, H. G. Dohlman, M. A. Bolanowski, R. A. F. Dixon, P. Keller, M. G. Caron, and R. J. Lefkowitz. 1996. Delineation of the intronless nature of the genes for the human and hamster $\beta_2$-adrenergic receptor end their promoter agonists; J. Biol. Chem.: 262:7321–7327.

14. Parola, A. L. and B. K. Kobilka. 1994. The peptide product of a 5' leader cistron in the beta 2 adrenergic receptor mRNA inhibits receptor synthesis. J Biol Chem 269:4497–4505.

15. Jones, A. S. 1963. Use of Alkyltrimethylammonium Bromide for the Isolation of Ribo- and Deoxyribo-nucleic Acid. Nature 199:280–282.

16. Nikiforov, T. T., R. B. Rendle, P. Goelet, Y.-H. Rogers, M. L. Kotewicz, S. Anderson, G. L. Trainor, and M. R. Knapp. 1994. Genetic Bit Analysis: a solid phase method for typing single nucleotide polymorphisms. Nucleic Acids Research 22:4167–417S.

17. McGraw, D. W., E. T. Donnelly, M. G. Eason, S. A. Green, and S. B. Liggett. 1998. Role of βARK in long-term agonist-promoted desensitization of the $\beta_2$-adrenergic receptor. Cell Signal 10:197–204.

18. McGraw, D. W. and S. B. Liggett. 1997. Heterogeneity in βARK expression in the lung accounts for cell-specific desensitization of the $\beta_2$-adrenergic receptor. J. Biol. Chem. 272:7338–7343.

19. Smith, P. K., R. I. Krohn, G. T. Hermanson, A K. Mallia, F. H. Gartner, M. D. Provenzano, E. K. Fujimoto, N. M. Goeke, B. J. Olson, and D. C. Klenk. 198S. Measurement of protein using bicinchoninic acid. Anal.Biochem. 150:76–85.

20. Calnan, B. J., B. Tidor, S. Biancalana, D. Hudson, and A. D. Frankel. 1991. Arginine-Mediated RNA Recognition: The Arginine Fork. Science 252:1167–1171.

21. Fedyk, E. R., A. A. Looney, and R. P. Phipps. 1996. Regulation of IgE and cytokine production by cAMP: implications for extrinsic asthma. Clin Immunol Immunopathol 81:101–113.

22. Themmen, A. P. N., J. W. M. Martens, and H. G. Brunner. 1997. Gonadotropin receptor mutations. J Endocrinol 153:179–183.

23. Chattopadhyay, N., A. Mithal, and E. M. Brown. 1996. The calcium-sensing receptor: a window into the physiology and pathophysiology of mineral ion metabolism. Endocr Rev 17:289–307.

24. Rosenthal, W. A. Antaramian, S. Gilbert, and M. Bimbaumer. 1993. Nephrogenic diabetes insipidus: a V2 vasopressin receptor unable to stimulate adenylyl cyclase. J. Biol. Chem. 268:13030–13033.

25. Gether, U., J. A. Ballesteros, R. Seifert, E. Sanders-Bush, H. Weinstein, and B. K. Kobilka. 1997. Structural instability of a constitutively active G protein-coupled receptor. J. Biol. Chem. 272:2587–2590.

26. Kotanko, P., A. Binder, J. Tasker, P. DeFreitas, S. Kamdar, A. J. Clark, F. Skrabal, and M. Caulfield. 1997. Essential hypertension in African Caribbean's associates with a variant of the beta2-adrenoceptor. Hypertension 30:773–776.

27. Large, V., L. Hellstrom, S. Reynisdottir, F. Lonnqvist, P. Eriksson, L. Lannfelt, and P. Amer. 1997. Human beta-2 adrenoceptor gene polymorphisms are highly frequent in obesity and associate with altered adipocyte beta-2 adrenoceptor function. J Clin Invest 100:3005–3013.

28. Thomson, J. A. et al. 1998. Embryonic Stem cell lines derived from human blastocysts. Science 282:1145–1147.

29. Yamada K, et al., 1999. Polymorphism in the 5'-leader cistron of the $\beta_2$-adrenergic receptor gene associated with obesity and type 2 diabetes. J. Clin. Endocrinol. & Metabol. 84:1754–1757, 1999.

What is claimed is:

1. A method for predicting a patient's bronchodilating response to an agonist of $\beta_2AR$, which comprises determining the patient's genotype for the $\beta_2AR$ 5'LC polymorphic site, wherein a patient who is homozygous T at this site is unlikely to exhibit a bronchodilating response to the agonist and a patient who contains a C at this site is likely to exhibit a bronchodilating response against the agonist.

2. The method of claim 1, wherein the agonist is albuterol.

* * * * *

SEQUENCE LISTING

<160> NUMBER OF SEQ ID NOS: 14

<210> SEQ ID NO 1
<211> LENGTH: 2340
<212> TYPE: DNA
<213> ORGANISM: Homo sapiens

<400> SEQUENCE: 1

```
cccggttca  agagattctc  ctgtctcagc  ctcccgagta  gctgggacta  caggtacgtg      60
ccaccacacc  tggctaattt  ttgtattttt  agtagagaca  agagttacac  catattggcc     120
aggatctttt  gctttctata  gcttcaaaat  gttcttaatg  ttaagacatt  cttaatactc     180
tgaaccatat  gaatttgcca  ttttggtaag  tcacagacgc  cagatggtgg  caatttcaca     240
tggcacaacc  cgaaagatta  acaaactatc  cagcagatga  aaggattttt  tttagtttca     300
ttgggtttac  tgaagaaatt  gtttgaattc  tcattgcatc  tccagttcaa  cagataatga     360
gtgagtgatg  ccacactctc  aagagttaaa  aacaaaacaa  caaaaaaatt  aaaacaaaag     420
cacacaactt  tctctctctg  tcccaaaata  catacttgca  tacccccgct  ccagataaaa     480
tccaaagggt  aaaactgtct  tcatgcctgc  aaattcctaa  ggagggcacc  taaagtactt     540
```

```
gacagcgagt gtgctgagga aatcggcagc tgttgaagtc acctcctgtg ctccttgccaa      600
atgtttgaaa gggaatacac tgggttaccg ggtgtatgtt gggaggggag cattatcagt      660
gctcgggtga ggcaagttcg gagtacccag atggagacat ccgtgtctgt gtcgctctgg      720
atgcctccaa gccagcgtgt gtttactttc tgtgtgtgtc accatgtctt tgtgcttctg      780
ggtgcttctg tgtttgtttc tggccgcgtt tctgtgttgg acaggggtga ctttgtgccg      840
gatggcttct gtgtgagagc gcgcgcgagt gtgcatgtcg gtgagctggg agggtgtgtc      900
tcagtgtcta tggctgtggt tcggtataag tctgagcatg tctgccaggg tgtatttgtg      960
cctgtatgtg cgtgcctcgg tgggcactct cgtttccttc cgaatgtggg gcagtgccgg     1020
tgtgctgccc tctgccttga cctcaagc cgcgcaggcg cccagggcag caggtagcg         1080
gccacagaag agccaaaagc tcccggttg gctggtaagg acaccacctc cagctttagc       1140
cctctggggc cagccagggt agccgggaag cagtggtggc ccgccctcca gggagcagtt     1200
gggccccgcc cgggccagcc ccaggagaag gagggcgagg ggaggggagg gaaaggggag     1260
gagtgcctcg ccccttcgcg gctgccggcg tgccattggc cgaaagttcc cgtacgtcac     1320
ggcgagggca gttcccctaa agtcctgtgc acataacggg cagaacgcac tgcgaagcgg     1380
cttcttcaga gcacgggctg gaactggcag gcaccgcgag ccctagcac ccgacaagct       1440
gagtgtgcag gacgagtccc caccacaccc acaccacagc cgctgaatga ggcttccagg     1500
cgtccgctcg cggccgcag agccccgccg tgggtccgcc cgctgaggcg ccccagcca       1560
gtgcgcttac ctgccagact gcgcgccatg gggcaacccg ggaacggcag cgccttcttg     1620
ctggcaccca atagaagcca tgcgccggac cacgacgtca cgcagcaaag ggacgaggtg     1680
tgggtggtgg gcatgggcat cgtcatgtct ctcatcgtcc tggccatcgt gtttggcaat     1740
gtgctggtca tcacagccat tgccaagttc gagcgtctgc agacggtcac caactacttc     1800
atcacttcac tggcctgtgc tgatctggtc atgggcctgg cagtggtgcc ctttggggcc     1860
gcccatattc ttatgaaaat gtggacttt ggcaacttct ggtgcgagtt ttggacttcc       1920
attgatgtgc tgtgcgtcac ggccagcatt gagaccctgt gcgtgatcgc agtggatcgc     1980
tactttgcca ttacttcacc tttcaagtac cagagcctgc tgaccaagaa taaggcccgg     2040
gtgatcattc tgatggtgtg gattgtgtca ggccttacct ccttcttgcc cattcagatg     2100
cactggtacc gggccaccca ccaggaagcc atcaactgct atgccaatga gacctgctgt     2160
gacttcttca cgaaccaagc ctatgccatt gcctcttcca tcgtgtcctt ctacgttccc     2220
ctggtgatca tggtcttcgt ctactccagg gtctttcagg aggccaaaag gcagctccag     2280
aagattgaca aatctgaggg ccgcttccat gtccagaacc ttagccaggt ggagcaggat     2340
```

```
<210> SEQ ID NO 2
<211> LENGTH: 60
<212> TYPE: DNA
<213> ORGANISM: Homo sapiens

<400> SEQUENCE: 2
atgaggcttc caggcgtccg ctcgcggccc gcagagcccc gccgtgggtc cgcctgctga      60

<210> SEQ ID NO 3
<211> LENGTH: 19
<212> TYPE: PRT
<213> ORGANISM: Homo sapiens

<400> SEQUENCE: 3

Met Arg Leu Pro Gly Val Arg Ser Arg Pro Ala Glu Pro Arg Arg Gly
```

```
                1               5              10              15
Ser Ala Cys

<210> SEQ ID NO 4
<211> LENGTH: 19
<212> TYPE: PRT
<213> ORGANISM: Homo sapiens

<400> SEQUENCE: 4

Met Arg Leu Pro Gly Val Arg Ser Arg Pro Ala Glu Pro Arg Arg Gly
  1               5              10              15

Ser Ala Arg

<210> SEQ ID NO 5
<211> LENGTH: 15
<212> TYPE: DNA
<213> ORGANISM: Homo sapiens

<400> SEQUENCE: 5
gtccgcccgc tgagg                                                    15

<210> SEQ ID NO 6
<211> LENGTH: 15
<212> TYPE: DNA
<213> ORGANISM: Homo sapiens

<400> SEQUENCE: 6
gtccgcctgc tgagg                                                    15

<210> SEQ ID NO 7
<211> LENGTH: 20
<212> TYPE: DNA
<213> ORGANISM: Homo sapiens

<400> SEQUENCE: 7
ccccgccgtg ggtccgcccg                                               20

<210> SEQ ID NO 8
<211> LENGTH: 20
<212> TYPE: DNA
<213> ORGANISM: Homo sapiens

<400> SEQUENCE: 8
ccccgccgtg ggtccgcctg                                               20

<210> SEQ ID NO 9
<211> LENGTH: 20
<212> TYPE: DNA
<213> ORGANISM: Homo sapiens

<400> SEQUENCE: 9
ggctgggggc gcctcagcgg                                               20

<210> SEQ ID NO 10
<211> LENGTH: 20
<212> TYPE: DNA
<213> ORGANISM: Homo sapiens

<400> SEQUENCE: 10
ggctgggggc gcctcagcag                                               20

<210> SEQ ID NO 11
```

-continued

```
<211> LENGTH: 23
<212> TYPE: DNA
<213> ORGANISM: Homo sapiens

<400> SEQUENCE: 11
aaggacacca cctccagctt tag                                          23

<210> SEQ ID NO 12
<211> LENGTH: 20
<212> TYPE: DNA
<213> ORGANISM: Homo sapiens

<400> SEQUENCE: 12
cgcatggctt ctattgggtg                                              20

<210> SEQ ID NO 13
<211> LENGTH: 20
<212> TYPE: DNA
<213> ORGANISM: Homo sapiens

<400> SEQUENCE: 13
gctgaatgag gcttccaggc                                              20

<210> SEQ ID NO 14
<211> LENGTH: 20
<212> TYPE: DNA
<213> ORGANISM: Homo sapiens

<400> SEQUENCE: 14
cgcatggctt ctattgggtg                                              20
```